Figure 1:
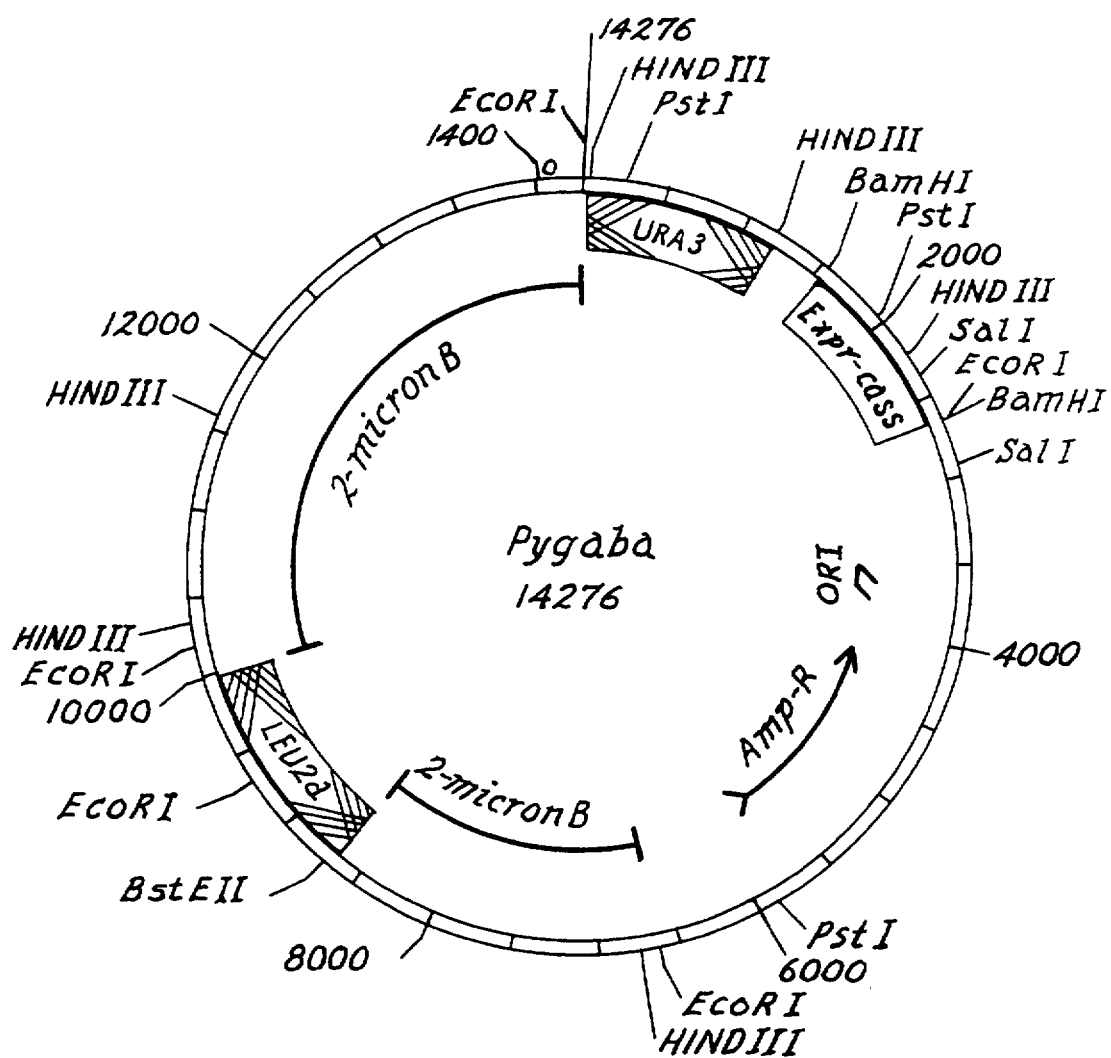

United States Patent [19]

Balschmidt et al.

[11] Patent Number: 5,430,016
[45] Date of Patent: Jul. 4, 1995

[54] INSULIN COMPOUNDS AND COMPOSITIONS

[75] Inventors: Per Balschmidt, Espergaerde; Finn B. Hansen, Roskilde, both of Denmark

[73] Assignee: Novo Nordisk A/S, Bagsvaerd, Denmark

[21] Appl. No.: 495,798

[22] Filed: Mar. 19, 1990

[30] Foreign Application Priority Data

Mar. 20, 1989 [DK] Denmark .................. 1341/89

[51] Int. Cl.$^6$ .................. A61K 37/26; C07K 7/40
[52] U.S. Cl. .................. 514/4; 514/3; 530/303; 530/305; 930/10
[58] Field of Search .................. 530/303; 514/3, 4; 435/68.1, 69.4

[56] References Cited

U.S. PATENT DOCUMENTS

| | | | |
|---|---|---|---|
| 4,400,465 | 8/1983 | Morihara et al. | 435/68.1 |
| 4,608,364 | 8/1986 | Grau | 514/4 |
| 4,701,440 | 10/1987 | Grau | 514/3 |
| 4,916,212 | 4/1990 | Marhussen | 435/69.4 |
| 4,946,828 | 8/1990 | Marhussen | 514/3 |
| 4,959,351 | 9/1990 | Grau | 514/3 |
| 5,008,241 | 4/1991 | Markussen et al. | 514/3 |
| 5,028,586 | 7/1991 | Balschmidt et al. | 514/3 |
| 5,028,587 | 7/1991 | Dorschug et al. | 514/3 |

OTHER PUBLICATIONS

Blundell et al., *Advances in Protein Chemistry*, 26:340–347 (Ed. Anifinsen, Edsall, Richards), 1972.
Weinert, M. et al., *Hoppe-Seyler's Z-Physiol. Chem.*, 352:719–724, 1971.
Zahn et al., "Molecular Basis of Insulin-action", 5th Anniversary Insulin Symposium, Indiana, Oct. 1971.
Smith, L., "Amino Acid Sequences of Insulin", Sec. III The Molecular Basis of Action, 5th Anniversary Insulin Symp. 1971.
Dayhoff, M., Atlas of Protein Sequence and Structure, vol. 5:89–99, 1972.
Creighton, T., *Proteins*, Watt. Freeman & Co., 1984, p. 428.

*Primary Examiner*—F. T. Moezie
*Attorney, Agent, or Firm*—Steve T. Zelson; Elias J. Lambiris

[57] ABSTRACT

Novel insulin compounds having a desirably protracted insulin action and/or antigenicity are provided.

The novel insulin compounds are represented by the formula II:

```
A-Chain
                        S ——————————— S
                        |  7                      |
H-Arg-Gly-Ile-Val-E-Gln-Cys-Cys-Thr-Ser-Ile-Cys-Ser-
  0   1   2   3  4  5   6   |  8   9  10  11  12
                            S
                            |
B-Chain                     S
                            |
H-Phe-Val-Asn-Gln-His-Leu-Cys-Gly-Ser-His-Leu-Val-
  1   2   3   4   5   6   7   8   9  10  11  12

A-Chain (contd.)
                          20
Leu-Tyr-Gln-Leu-E-Asn-Tyr-Cys-N—OH
 13  14  15  16 17  18  19  | 21
                            ┌─S
                            |
B-Chain (contd.)            S
                            |
E-Ala-Leu-Tyr-Leu-Val-Cys-Gly-E-Arg-Gly-Phe—
 13  14  15  16  17  18  19 20 21  22  23  24

B-Chain (contd.)
Phe-Tyr-T-Pro-Lys-X—Y
 25  26 27 28  29 30
``` wherein

E individually represents Glu or a neutral amino acid residue which can be coded for by nucleotide sequences, N represents an amino acid residue which can be coded for by nucleotide sequences, T represents Thr or Arg, X represents Thr, Ser, Ala or OH, and Y represents OR or NR$^1$R$^2$, where R, R$^1$ and R$^2$ individually represents hydrogen or lower alkyl, but is not present when X represents OH.

18 Claims, 3 Drawing Sheets

INSULIN COMPOUNDS AND COMPOSITIONS

The present invention relates to novel insulin compounds, to a process for preparing the novel insulin compounds and to therapeutic preparations showing protracted action and comprising at least one of the novel insulin compounds and, if desired, a fast acting insulin.

Ever since the discovery of insulin in 1922 many different types of insulin preparations have been used for the treatment of Diabetes mellitus. At the beginning, exclusively insulin solutions exhibiting a rapidly commencing and relatively rapidly ceasing insulin activity were used, but later on insulin preparations exhibiting a wider profile of activity by lovering the solubility of insulin by means of additions of e.g. zinc salt and/or protamines were developed. Due to availability the insulin used herefor has traditionally normally been extracted from Pancreas from domestic animals, most frequently oxes, pigs and sheep. However, recently preparations containing human insulin of biotechnological origin have also appeared on the market.

The structure of human insulin is shown in formula I.

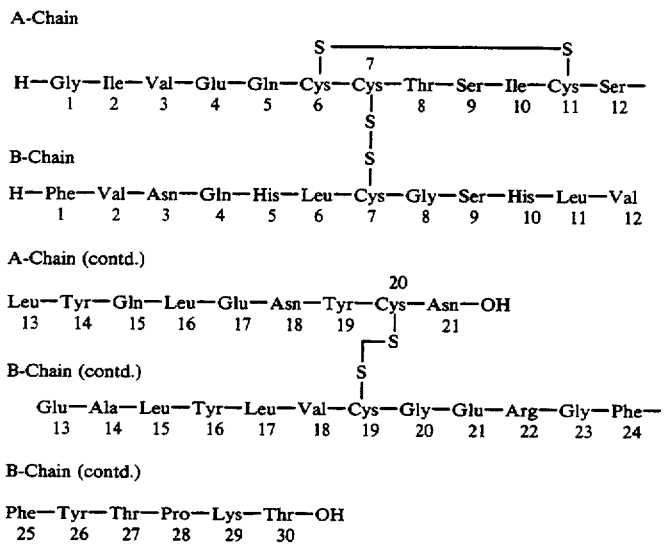

The insulins from certain domestic animals are very similar in structure to human insulin. Dog and pig insulin only differs from human insulin by containing Ala rather than Thr in position 30 in the B-chain and rabbit insulin only by containing Ser in the same position. These insulins may be converted into human insulin by replacement of the B30-amino acid residue with Thr by semisynthetic procedures as described e.g. by Morihara et al, Nature 280 (1979), 412-13 and Marcussen (U.S. Pat. No. 4,343,898).

Preparations containing insulin in solution are usually rapid acting, the insulin activity ceasing a few hours after injecting. Hence, it is necessary to give frequent injections, normally several times a day, to normalize the blood glucose level in the diabetic.

In order to overcome this disadvantage insulin preparations with protracted action have been formulated so that insulin activity is maintained for several hours, even up to 24 hours or even longer. Using such protracted preparations some diabetic patients only have to receive a small number of daily injections, e.g. one or two injections during 24 hours.

Such a protracted action can be achieved by converting the insulin to a slightly soluble salt, such as zinc insulin or protamin insulin. The slightly soluble insulin salts are used in the form of suspensions from which the insulin is gradually released after subcutaneous or intramuscular injection.

Recently other methods have been invoked to achieve a protracted action. An example hereof is the encapsulation of insulin crystals in polymerized serum albumin. Another example is continuously acting infusion devices, so-called insulin pumps, which however may be uncomfortable and entail a risk to the patient.

The specifications of European Patent Publications Nos. EP 132770, EP 132769 and EP 135720 disclose the preparation and use of insulin derivatives wherein the C-terminus of the B-chain is extended with an organic group carrying at least one positive charge, preferably Arg-OH or Arg-Arg-OH. Preparations containing suspensions of such insulin derivatives exhibit protracted action. However, these insulin compounds are not very suitable in formulating novel useful protracted insulin preparations because the degree of protraction has been found to be very limited (J. Markussen et al.: Protein Engineering 1, 205-213 (1987).

The properties of insulin derivatives wherein the N-terminus of the B-chain is extended with the dipeptide Arg-Arg has been described by R. Geiger & F. Enzmann in: Proceedings of the Symposium on Proinsulin, Insulin and C-peptide, Tokushima 1978; Excerpta, Medica, Amsterdam 1979, p. 306-310. The solubility of this insulin compound around its isoelectric point was found to be even higher than that of normal insulin.

Substitutions in the insulin molecule can be introduced with the purpose of improving the profile of activity of the insulin in the treatment of Diabetes. Thus, European Patent Publication No. EP 194864 discloses that one or more substitutions of Glu with e.g. Gln and/or substitution of $Thr^{B27}$ with Arg combined with a blocking of the C-terminal carboxyl group in the form of ester or amide causes a shifting of the zone of precipitation of the insulin in such a manner that a slow release after injection is obtained.

The use of this kind of insulin compounds containing internal amino acid substitutions in preparations for the lifelong treatment of Diabetes implies a substantial risk of activating the immune system of the patient causing introduction of insulin antibodies in the blood.

Within the last few years several attempts have been made to find substitutions for the traditional insulin preparations with protracted insulin action. The reasons for this are that diabetologists have found the traditional protracted insulin preparations to be too short acting, especially after the introduction of the human insulin and that the introduction of the so-called insulin pen has called for a dissolved protracted acting insulin.

The object of the invention is to provide novel insulin analogues which exhibit a protracted insulin action, and which present as low antigenecity as possible It has now surprisingly been found that insulin compounds having the general formula II

```
A-Chain        S ───────────── S
               |  7             |
H-Arg-Gly-Ile-Val-E-Gln-Cys-Cys-Thr-Ser-Ile-Cys-Ser-
  0   1   2   3   4  5   6   7   8   9   10  11  12
                             |
                             S
B-Chain                      |
                             S
                             |
H-Phe-Val-Asn-Gln-His-Leu-Cys-Gly-Ser-His-Leu-Val-
  1   2   3   4   5   6   7   8   9   10  11  12
```

A-Chain (contd.)
```
                          20
Leu-Tyr-Gln-Leu-E-Asn-Tyr-Cys-N—OH
 13  14  15  16 17 18  19  |  21
                           ┌─S
                           |
B-Chain (contd.)           S
                           |
E-Ala-Leu-Tyr-Leu-Val-Cys-Gly-E-Arg-Gly-Phe—
13  14  15  16  17  18  19 20 21  22  23  24
```

B-Chain (contd.)

Phe-Tyr-T-Pro-Lys-X—Y
25  26  27 28  29  30 wherein

E individually represents Glu or a neutral amino acid residue which can be coded for by nucleotide sequences, N represents an amino acid residue which can be coded for by nucleotide sequences, T represents Thr or Arg, X represents Thr, Ser, Ala or OH, and Y represents OR or $NR^1R^2$, where R, $R^1$ and $R^2$ individually represents hydrogen or lower alkyl, but is not present when X represents OH, exhibit a desirably protracted insulin action and/or antigenicity.

Accordingly, the invention relates to insulin compounds having the general formula II:

```
A-Chain        S ───────────── S
               |  7             |
H-Arg-Gly-Ile-Val-E-Gln-Cys-Cys-Thr-Ser-Ile-Cys-Ser-
  0   1   2   3   4  5   6   7   8   9   10  11  12
                             |
                             S
B-Chain                      |
                             S
                             |
H-Phe-Val-Asn-Gln-His-Leu-Cys-Gly-Ser-His-Leu-Val-
  1   2   3   4   5   6   7   8   9   10  11  12
```

A-Chain (contd.)
```
                          20
Leu-Tyr-Gln-Leu-E-Asn-Tyr-Cys-N—OH
 13  14  15  16 17 18  19  |  21
                           ┌─S
                           |
B-Chain (contd.)           S
                           |
E-Ala-Leu-Tyr-Leu-Val-Cys-Gly-E-Arg-Gly-Phe—
13  14  15  16  17  18  19 20 21  22  23  24
```

B-Chain (contd.)

Phe-Tyr-T-Pro-Lys-X—Y
25  26  27 28  29  30 wherein E individually represents Glu or a neutral amino acid residue which can be coded for by nucleotide sequences, N represents an amino acid residue which can be coded for by nucleotide sequences, T represents Thr or Arg, X represents Thr, Ser, Ala or OH, and Y represents OR or $NR^1R^2$, where R, $R^1$ and $R^2$ individually represents hydrogen or lower alkyl, but is not present when X represents OH.

In the present context "lower alkyl" is intended to comprise straight or branched alkyl groups having 1-6 carbon atoms.

The invention relates in particular to insulin compounds of the formula II, wherein each E individually represents Glu or Gln, N represents Asn, Asp, Ser or Gly, T represents Thr or Arg, X represents Thr and Y represents $NH_2$.

The invention preferably relates to insulin compounds of the formula II wherein at least one of the symbols E, N, and T represents an amino acid residue different from the corresponding residue of human insulin when Y represent OH.

The invention relates specifically to insulin compounds of the formula II, wherein all E represents Glu, N represents Asn, T and X both represents Thr, and Y represents $NH_2$.

The invention relates specifically to insulin compounds of the formula II, wherein E all represents Glu, N represents Ser, R and X both represents Thr and Y represents $NH_2$.

The invention relates specifically to insulin compounds of the formula II, wherein E in position B13 represents Gln and the remaining E all represents Glu, N represents Asn, T and X both represent Thr and Y represents $NH_2$.

The invention relates specifically to insulin compounds of the formula II, wherein E in position A4 represents Gln and the remaining E all represents Glu, N represents Asp, T and X both represent Thr and Y represents $NH_2$.

The invention relates specifically to insulin compounds of the formula II, wherein E all represents Glu, N represents Asn, T represents Arg and X represents OH.

The invention also relates to a method for preparing insulin compounds of the formula II by which an insulin precursor of the general formula III:

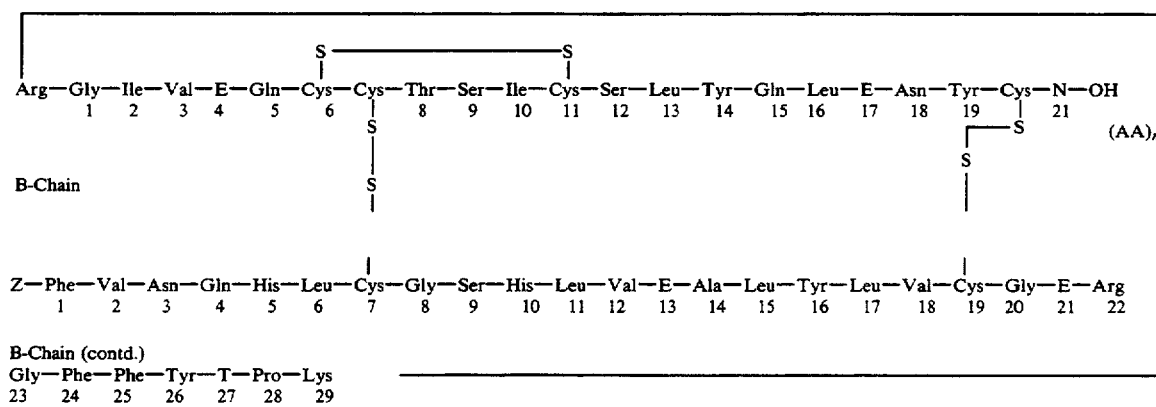

wherein E, N and T all have the same meaning as stated above, (AA)n represents a peptide chain having n amino acid residues having Lys as the C-terminal residue, or is a peptide bond when n=0, and Z represents hydrogen or a peptide chain of arbitrary length having Lys as the C-terminal residue, is transpeptidated or cleaved by an endopeptidase having exclusive specificity for cleavage at the carboxy side of a lysine residue.

The invention also relates to insulin preparations comprising at least one insulin compound of the formula II, and optionally also a fast acting insulin, such as human insulin, domestic animal insulin or derivatives or analogues thereof. Such preparations may be in the form of a solution ready for use or a lyophilized preparation to be reconstituted using e.g. sterilized water before use.

A particularly advantageous embodiment of the insulin preparation of the invention is a preparation for parenteral administration exhibiting protracted insulin action and comprising a solution of at least one insulin compound of the invention in an aqueous medium being isoosmotic with blood serum, having a pH between 2 and 5.5 and optionally containing a buffer and/or a preserving agent and, if desired, a fast acting insulin.

The insulin compounds of the invention fulfil the demands of the diabetologists through minimal changes in the human insulin molecule, each per se being either familiar to the human body or tested through several years and in this way not found to trigger an immune response. The main feature of the insulin compounds of the invention is that they can be described as human insulin wherein an arginine residue has been attached to the N-terminal end of the A-chain and where the C-terminal carboxylic group of the B-chain preferably has been blocked in form of the amide. The insulin compounds are intended to be used as dissolved in a weakly acidic solution and under these conditions substantial deamidation of the asparagin residue in position A21 can occur within the shelf life of the preparation of thus counteract the prolonged action. By introducing a substitution of one or possibly two of the glutamic acid residues with glutamine this effect can be controlled.

In the case of Insulin-Dependent Diabetes a frequently used therapy consists in two daily injections of a protracted insulin preparation, one in the morning and one in the evening just before bedtime, in order to create a basal insulin level. Additionally, three injections of a fast acting insulin preparation are given prior to the principal meals. The disadvantage of this therapy is that the late injection of the protracted preparation may result in a dangerously low blood glucose level in the course of the night. This may be avoided by injecting a mixed preparation of a protracted and a fast acting insulin before dinner, whereby hypoglycemia will, if at all, occur during the evening, where it can be averted by means of e.g. a light snack. However, this type of the therapy often results in hyperglycemia in the morning, as the mostly used protracted insulin preparations "Insulatard" ® and "Monotard" ® do not act for a sufficiently long time. Hence, there is a need to provide diabetic patients with insulin preparations acting longer than the preparations commonly in use, in particular if one injection of such a preparation will suffice for one or even several days. Insulin preparations prepared according to the invention exhibit a protracted insulin action of longer duration than that of the commonly used protracted insulin preparation "Monotard" ®.

The preferred insulin compounds of the invention are particularly advantageous for use in solution preparations, because the solubility is high, even around pH 5 (at which pH the deamidation is substantially lowered), and still exhibit pronounced protracted action after subcutaneous injection.

The invention relates in particular to the following specific compounds: [Arg$^{40}$]-human insulin- (B30-amide) [Arg$^{40}$,Gln$^{B13}$]-human insulin- (B30-amide) [Arg$^{40}$,Gln$^{44}$, Asp$^{A21}$]-human insulin- (B30-amide) [Arg$^{40}$,Ser$^{A21}$]-human insulin- (B30-amide) [Arg$^{40}$,Arg$^{B27}$]-des[Thr$^{B30}$]-human insulin.

The insulin compounds of the invention can be prepared from other insulins by introducing the additional arginin residue on the N-terminal of the A-chain of the insulin molecule by chemical synthesis, but only with great difficulties. A far more attractive route is the enzymatically catalyzed conversion of a single chain precursor, e.g. a naturally occurring proinsulin or preproinsulin or a biosynthetically prepared precursor of the general formula III:

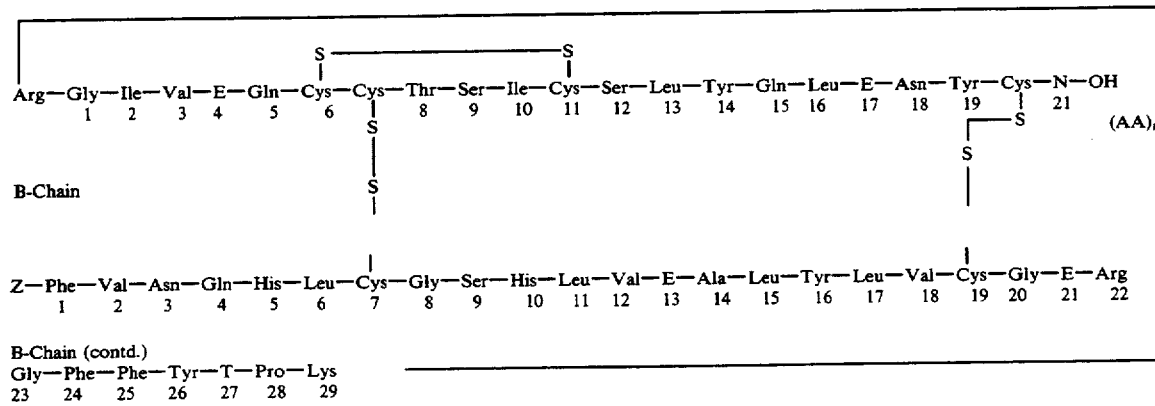

wherein

E, N and T all have the same meaning as stated under formula II, (AA)n represents a peptide chain with n amino acid residues and having Lys as the C-terminal residue, but is a peptide bond when n=0, and Z represents hydrogen or a peptide chain of arbitrary length having Lys as the C-terminal residue.

The enzyme used for the enzymatic convertion should be a trypsin-like endopeptidase capable of cleaving a peptide chain at the carboxy side of a lysine residue. Trypsin itself can often be used, but an endopeptidase exhibiting lysine specificity, e.g. endoproteinase Lys-C from Lysobacter enzymogenes (Boehringer Mannheim) or Lysyl endopeptidase from Achromobacter lyticus (Wako Pure Chemical Industries, Ltd.) is particularly advantageous.

The reaction can be performed as a transpeptidation using threonine amide under similar conditions as described in e.g. European Patent Publication No. EP 163529 and thus resulting directly in the B30-amide, but it can also be performed as a two-step reaction, starting with an enzymatic cleavage resulting in the des(Thr$^{B30}$)-compound which can be converted into the B30-amide by a coupling reaction as described by Morihara et al., loc.cit.

The precursors of the insulin compounds of the invention can be produced biosynthetically in a yeast host expressing a DNA-sequence encoding the precursor.

To achieve secretion to the growth medium, the DNA-sequence encoding the insulin precursor can be fused to another DNA-sequence encoding a signal peptide functional in yeast. Secretion can be achieved by insertion in the expression plasmid of the Saccharomyces cerevisiae MFα1-leader sequence (Kurjan & Herskowitz, Cell 30, 933–943 (1982)). In a preferred construction the DNA-sequence encoding the entire MFα1-leader sequence including the dibasic site LysArg but excluding the peptide sequence GluAla-GluAla being the substrate for the yeast protease DPAP (dipeptidyl aminopeptidase) is used. In this way, an efficient secretion of insulin precursors having the correct N-terminal is achieved.

DNA-sequences encoding modified insulin precursors were constructed by carrying out in vitro mutagenesis on the expression cassette which is contained in the BamHI restriction fragment from the expression plasmid pYGABA as shown in FIG. 1. The plasmid contains selection markers and replication signals functional in yeast and has a length of 1103 basepairs. The BamHI fragment contains the following: The GAPDH (glyceraldehyde-3-phosphate dehydrogenase) upstream region containing the promoter-sequences from position −389 to −1 according to Bitter & Egan, Gene 32, (1984) 263–274. To the 5'-end of the upstream region BamHI linkers were added. This promoter sequence is fused directly to the sequence described by Kurjan & Herskowitz encoding the 85N-terminal amino acids of the MFα1-leader sequence. The MFα1-leader sequence is fused directly to the coding sequence for the insulin precursor single chain des[Thr$^{B30}$]-human insulin (SCI), which is a synthetically constructed gene with the sequence:

```
TTCGTTAACCAACACTTGTGTGGTTCTCACTTGGTTGAAGCTTTGTACTTGGTTTGTGGT—
AAGCAATTGGTTGTGAACACACCAAGAGTGAACCAACTTCGAAACATGAACCAAACACCA—
Phe Val Asn Gln His Leu Cys Gly Ser His Leu Val Glu Ala Leu Tyr Leu Val Cys Gly—

GAAAGAGGTTTCTTCTACACTCCAAAGGGTATTGTTGAACAATGTTGTACTTCTATTTGT—
CTTTCTCCAAAGAAGATGTGAGGTTTCCCATAACAACTTGTTACAACATGAAGATAAACA—
Glu Arg Gly Phe Phe Tyr Thr Pro Lys Gly Ile Val Glu Gln Cys Cys Thr Ser Ile Cys—

SalI
TCTTTGTACCAATTGGAAAACTACTGTAACTAATAGCGTCG
AGAAACATGGTTAACCTTTTGATGACATTGATTATCGCAGCAGCT
Ser Leu Tyr Gln Leu Glu Asn Tyr Cys Asn End End
```

Also shown is that the translation of the insulin precursor gene is terminated with two stop-codons, and immediately after, a SalI restriction site is positioned. The terminator region is identical to the SalI-BamHI restriction fragment described in European Patent Publication No. 0 116 201 A1. The sequence is constructed using entirely standard techniques.

The mutagenesis method employed was "oligonucleotide site directed mutagenesis", which is described by Zoller & Smith, DNA, Vol. 3, No. 6, 479–488 (1984). The method is briefly described in the following, and is described more in detail in Example 1. Isolated from the expression plasmid the insulin precursor sequence is inserted into a single-stranded, circular M13 bacteriophage vector. To the single-stranded genom, a chemically synthesized complementary DNA-strand is annealed. The DNA-strand contains the desired sequence surrounded by sequences completely homologous to insulin sequences on the circular DNA. In vitro, the primer is then extended in the entire length of the circular genom biochemically using Klenow polymerass. This strand will give rise to single-stranded phages which, when grown in E. coli, give the possibility of isolating double-stranded DNA having the desired sequence. From this double-stranded DNA, a restriction fragment can be isolated and reinserted into the expression vector.

Figure 2:
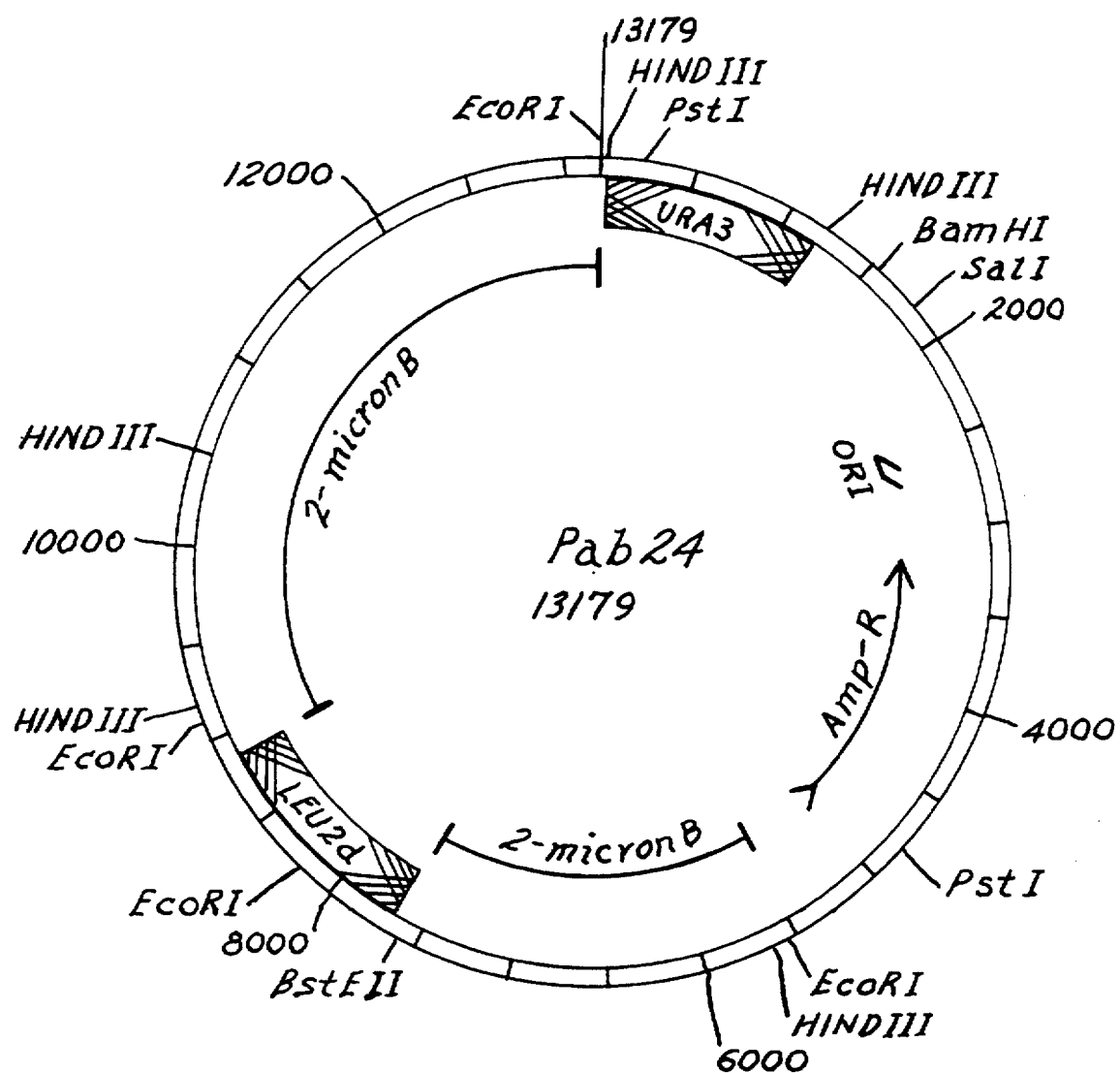
Figure 3:
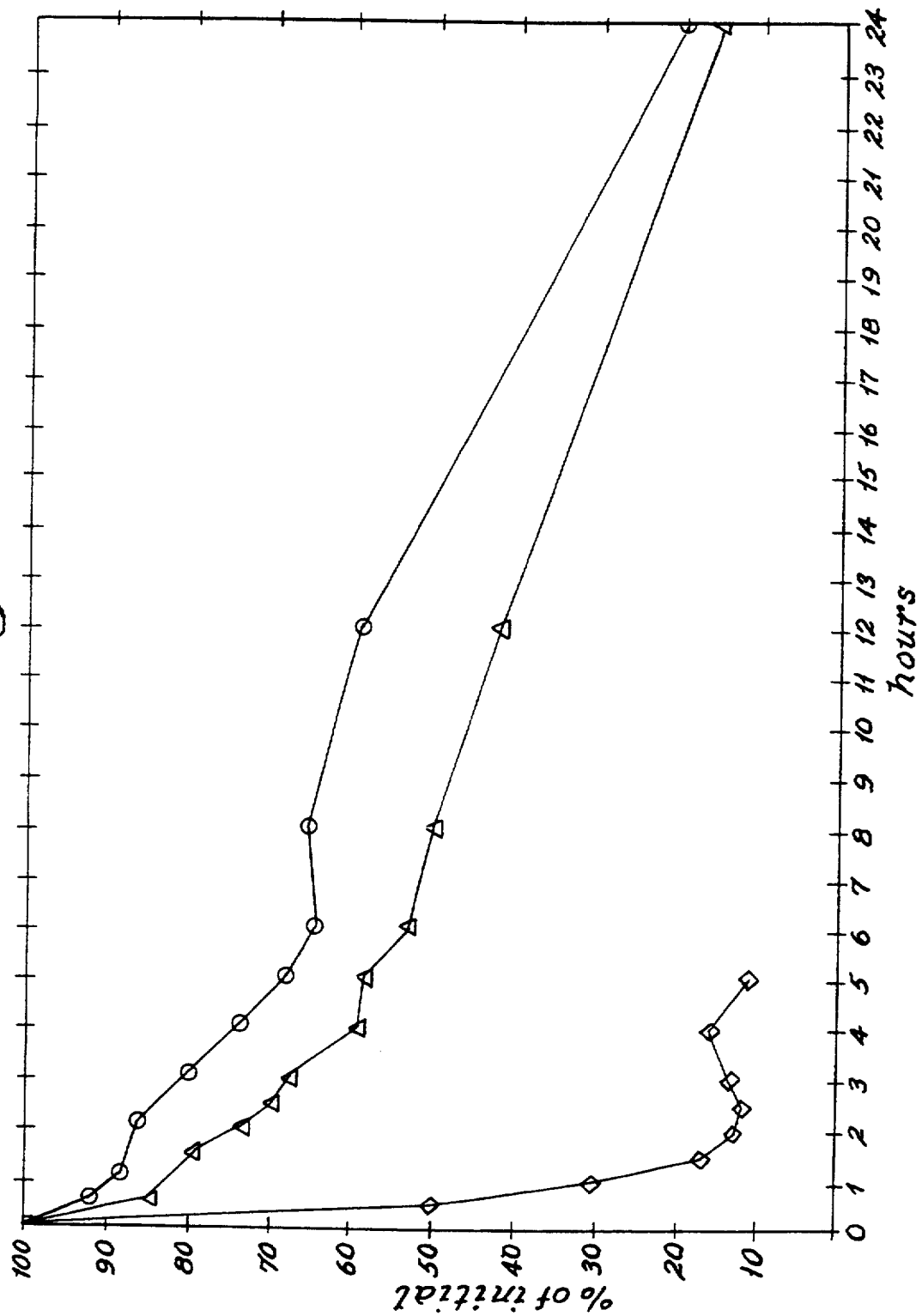

The invention is explained more in detail below with reference to the drawings in which FIG. 1 shows the expression plasmid pYGABA 14276, FIG. 2 shows the yeast vector pAB24, and FIG. 3 shows a graphical representation of the absorption of insulin from a subcutaneous depot.

The invention is further illustrated by the following Examples

EXAMPLE I

Construction of an expression plasmid, which can be used to express the precursor B(1–29)-AKR-A(1–21). The expression cassette, which is contained in the expression plasmid pYGABA (shown in FIG. 1) on a BamHI restriction fragment, was isolated: The expression plasmid was incubated with the restriction endonuclease BamHI. The conditions were: 20 μg of plasmid, 50 units of BamHI, 100 mM NaCl, 50 mM Tris-HCl, pH 7.5, 10 mM MgCl$_2$, and 1 mM DTT in a volume of 100 μlitres. The temperature was 37° C. and the reaction time 2 hours. The two DNA-fragments were separated on a 1% agarose gel, and the desired fragment was isolated.

Ligation on the M13 vector M13mp18:

The isolated restriction fragment was ligated to the bacteriophage vector M13mp18 also cut with the restriction endonuclease BamHI in the following reaction mixture: Fragment 0.2 μg, vector 0.02 μg, 50 mM Tris-HCl, pH 7.4, 10 mM MgCl$_2$, 10 mM DTT and 1 mM ATP in a volume of 20 μlitres. 5 μlitres of this mixture were transformed into the E. coli strain JM101. The presence of fragment in the vector and the orientation of the fragment was determined by restriction enzyme mapping on double-stranded M13-DNA isolated from the transformants.

Isolation of single-stranded (ss) DNA (template):

From the transformant described above ss-DNA was isolated according to a method described by Messing in Gene, 19, 269–276 (1982).

5'phosphorylation of the mutagenisation primer:

The mutagenisation primer having the sequence 5'-CAACAATACCTCTCTTAGCCTTTGGAGTG-3' was phosphorylated in the 5'end in a 30 μlitres reaction mixture containing 70 mM Tris-HCl, pH 7.0, 10 mM MgCl$_2$, 5 mM DTT, 1 mM ATP, 100 pmol oligonucleotide and 3.6 units of T4 polynucleotide kinase. The reaction was carried out for 30 min. at 37° C. Then the enzyme was inactivated by incubating the mixture for 10 min. at 65° C.

Annealing of template and phosphorylated mutagenisation primer:

Annealing of template and primer was carried out in a 10 μlitres volume containing 0.5 pmol template, 5 pmol primer, 20 mM Tris-HCl, pH 7.5, 10 mM MgCl$_2$, 50 mM NaCl and 1 mM DTT by heating for 10 min. at 65° C. and cooling afterwards to 0° C.

Extension/litigation reaction:

To the reaction mixture obtained above, 10 μlitres of the following mixture were added; 0.3 mMdATP, 0.3 mM dCTP, 0.3 mM dGTP, 0.3 mM TTP, 1 mM ATP, 20 mM Tris-HCl, pH 7.5, 10 mM MgCl$_2$, 10 mM DTT, 3 units of T4 DNA ligase and 2.5 units of Klenow polymerase. Then, the reaction was carried out for 16 hours at 16° C.

Transformation of JM101:

The above reaction mixture was transformed in different dilutions into CaCl$_2$-treated E. coli JM101 cells using standard techniques and plated in 2×YT topagar on 2×YT agar plates. (2×YT=tryptone 16 g/litre, yeast extract 10 g/litre, NaCl 5 g/litre. 2×YT topagar=2×YT with 0.4% agarose added and autoclaved. 2×YT agar plates=2×YT with 2% agar added and autoclaved). The plates were incubated at 37° C. overnight.

Identification of positive clones:

The method used was plaque-lift hybridisation which is described in the following: a nitrocellulose-filter was placed on a plate with a suitable plaque-density, so that the filter was wetted. The filter was then bathed in the following solutions: 1.5 M NaCl, 0.5M NaOH for 30 sec., 1.5M NaCl, 0.5 M Tris-HCl, pH 8.0 for 1 min., 2×SSC (0.3M NaCl, 0.03M sodium citrate) till later use. The filter was dried on 3MM filter paper and baked for 2 hours at 80° C. in a vacuum oven.

The mutagenisation primer having the sequence 5'-CAACAATACCTCTCTTAGCCTTTGGAGTG-3' was labelled radioactively in the 5'-end in a 30 μlitres volume containing 70mM Tris-HCl, pH 7.5, 10 mM MgCl$_2$, 5 mM DTT, 10 pmol oligonucleotide, 20 pmol gamma-$^{32}$p-ATP and 3.5 units of T4 polynucleotide kinase. The mixture was incubated at 37° C. for 30 min. and then for 5 min. at 100° C.

The dried filter was prehybridised for 2 hours at 65° C. in 6×SSC, 0.2% bovine-serum albumin, 0.2% Ficoll, 0.2% polyvinylpyrrolidon, 0.2% sodium-dodecyl-sulphate (SDS) and 50 μg/ml salmon-sperm DNA. Then, the reaction mixture containing the labelled probe was added to 15 ml of fresh prehybridisation mix, and the filter was bathed herein overnight at 40° C. with gentle shaking. After hybridisation, the filter was washed 3 times for each 15 min. in 2×SSC+0.1% SDS and autoradiographed. After wash in the same solution, but now at 62° C., and another autoradiography, plaques containing DNA-sequences complementary to the mutagenisation primer were identified.

Re-screening of positive clones:

Because the identified clone is a result of a heteroduplex, the plaque was plated again. The hybridisation and identification were repeated.

Purification of double-stranded M13-phage DNA.

A re-screened clone was used for infection of the E. coli strain JM101. A culture containing approximately 10$^8$ phages and 5 colonies of JM101 was grown for 5 hours in a 5 ml 2×YT medium at 37° C. Then, double-stranded, circular DNA was purified from the pellet according to a method described by Birnboim & Doly, Nucleic Acids Res., 2, 1513 (1979).

Isolation of a restriction fragment containing modified insulin precursor:

The DNA-preparation (appr. 5 μg) isolated above was digested with 10 units of the restriction endonuclease BamHI in 60 μlitres of 100 mM NaCl, 50 mM Tris-HCl, pH 7.5, 10 mM MgCl$_2$, and 1 mM DTT for 2 hours at 37° C. The DNA-products were separated on an agarose-gel, and the fragment was purified from the gel.
Ligation to the yeast vector pAB24 (FIG. 2):

The isolated restricted fragment was ligated to the yeast vector pAB24 digested with the restriction endonuclease BamHI in the following reaction mixture: Fragment 0.2 μg, vector 0.02 μg, 50 mM Tris-HCl, pH 7.4, 10mM MgCl$_2$, 10 mMDTT, 1 mMATP in a total volume of 20 μlitres. 5 μlitres of this reaction mixture was used for transformation of the E. coli strain MC1061, in which the modified expression plasmid was identified and propagated. The plasmid was called pYGAB-AKR-A and was identical to pYGABA, except for the added codon.

Transformation of yeast:

Transformation of the expression plasmid into the yeast strain Saccharomyces cerevisiae JC482/\ pep/- \ Leu2cir° (a,his4, pep4, ura3, leu2, cir°) was carried out as described by Ito et al., J. Bact. Vol. 153, No. 1, 163-168 (1983). The transformed cells were plated on SC-ura medium (0.7% Yeast Nitrogen Base, 2.0% glucose, 0.5% casamino acids, 2.0% agar) for selection for plasmid-containing cells.

EXAMPLE II

Construction of an expression plasmid, which can be used for production of the precursor B(1-29)-Gly-Ser-Lys-Arg-A(1-21).

The procedure used was essentially the same as described in example I, except that the mutagenisation primer had the sequence 5'CAACAATACCTCTCT-TAGAACCCTTTGGAGTG-3', that the hybridization temperature was 42° C., and that the washing temperature after hybridization was 64° C. The modified plasmid has a sequence identical to pYGABA, except for the added codons.

EXAMPLE III

Construction of an expression plasmid, which can be used for production of the precursor [Gln$^{B13}$]-B(1-29)-Ala-Lys-Arg-A (1-21).

The procedure used was essentially the same as described in example I, except that the template used was obtained by cloning the BamHI-cassette from pYGAB-AKR-A in M13, that the mutagenisation primer had the sequence 5'-GTACAAAGCTTGAACCAAGTG-3', that the hybridization temperature was 31° C., and that the washing temperature after hybridization was 53° C. The modified plasmid has a sequence identical to pYGABA, except for the altered and added codons.

EXAMPLE IV

Construction of an expression plasmid, which can be used for production of the precursor [Gln$^{44}$,Asp$^{421}$]-B(1-29)-Ala-Lys-Arg-A(1-21).

The procedure used was essentially the same as described in example I, except that the template used was obtained by cloning the BamHI-cassette from pYGAB-AKR-A in M13 and that the mutagenesis was made in two steps. In step 1 the primer was 5'-ACAACATTGTTGAACAATACC-3', the hybridization temperature was 27° C. and the washing temperature after hybridization was 49° C. and in step 2 the primer was 5'-CGCTATTAGTCACAGTAGTTT-3', the hybridization temperature was 29° C. and the washing temperature after hybridization was 51° C. The modified plasmid has a sequence identical to pYGABA, except for the altered and added codons.

EXAMPLE V

Construction of an expression plasmid, which can be used for production of the precursor [Ser$^{421}$]-B(1-29)-Ala-Lys-Arg-A(1-21).

The procedure used was essentially the same as described in example I, except that the template used was obtained by cloning the BamHI-cassette from pYGAB-AKR-A in M13, that the mutagenisation primer had the sequence 5'-GACGCTATTAAGTACAGTAGT-3', that the hybridization temperature was 29° C., and that the washing temperature after hybridization was 51° C. The modified plasmid has a sequence identical to pYGABA, except for the altered and added codons.

EXAMPLE VI

Construction of an expression plasmid, which can be used for production of the precursor [Arg$^{B27}$]-B(1-29)-Ala-Lys-Arg. A(1-21).

The procedure used was essentially the same as describe in example I, except that the template used was obtained by cloning the BamHI-cassette from pYGAB-AKR-A in M13, that the mutagenisation primer had the sequence 5'-CAACAATACCTCTCT-TAGCCTTTGGTCTGTAGAAGA-3', that the hybridization temperature was 43° C., and that the washing temperature after hybridization was 65° C. The modified plasmid has a sequence identical to pYGABA, except for the altered and added codons.

EXAMPLE VII

Expression of precursor and isolation from the culture medium.

Yeast, transformed as described in examples I to VI was propagated on Petri-plates containing minimal-medium without uracil for 48 hours at 30° C. 100 ml shake bottles containing minimal-medium without uracil +5 g/litre casamino acids +10 g/litre succinic acid +30 g/litre glucose at pH 5.0 were inoculated with a single colony from the Petri-plate. The bottles were then shaken at 30° C. in incubator for 72 hours.

After centrifugation 1 litre of pooled supernatant was sterilized by filtration and adjusted to pH 4-4.5 and a conductivity <10 mS by addition of 5 M HCl and water. Using a flow of 120 ml/hour the supernatant was then applied to a 1.6×6 cm column of S-Sepharose ®FF previously equilibrated with 50 mM acetic acid, 50% (by volume) ethanol adjusted to pH 4.0 with NaOH. The column was washed with 60 ml buffer and the precursor was eluted by a linear gradient of NaCl from 0 to 0.35M in 360 ml buffer with a flow of 10 ml/hour. The eluate was divided in fractions of 4 ml and detected for UV-absorbance. Fractions containing precursor were identified by RP-HPLC analysis and were pooled. After desalting on a column of Sephadex ® G25 in 1M acetic acid the precursor was isolated by lyophilization.

EXAMPLE VIII

Preparation of [Arg$^{A0}$]-des[Thr$^{B30}$]-human insulin from the precursor B(1-29)-Ala-Lys-Arg-A(1-21).

250 mg of B(1-29)-Ala-Lys-Arg-A(1-21), prepared by the methods described in examples I and VII, were dissolved at 4° C. in 25 ml of 50 mM tris-(hydroxymethyl)aminomethane, 20% (by volume) ethanol adjusted to pH 10 with HCl. Sepharose ® containing 0.8 mg of immobilized trypsin/ml was washed on a glass filter with the same buffer and was drained. Buffer was added to 40 g of drained gel and the volume was adjusted to 75 ml. The solution containing the precursor was added to the suspension and the mixture was left for one hour at 4° C. with gentle agitation and was then filtered.

HPLC-analysis shows 61% conversion to [Arg$^{A0}$]-des-[Thrs$^{B30}$]-human insulin.

The gel was washed with 50 ml of buffer (without ethanol) and drained, and the proteins in the pooled filtrates were precipitated by adjusting the pH to 6. The precipitate was isolated by centrifugation and lyophilization.

The precipitate was dissolved at 4° C. in 20 ml 7M urea by adjusting the pH to 8.1 and the solution was applied to a 1.6×20 cm column of Q-Sepharose ®FF previously equilibrated at 4° C. in 20mMtris-(hydroxymethyl)aminomethane, 7M urea adjusted to pH 8.1 with HCl. Using a flow of 40 ml/hour the column was then eluted with a linear gradient from 0 mM to 50 mM NaCl in the same buffer over 24 hours. The eluate was detected by UV-absorption and the first eluting of the two main peaks was collected. The pool was desalted in 1M acetic acid on a column of Sephadex ® G25 and was lyophilized. The yield was 75 mg of [Arg$^{A0}$]-des[Thr$^{B30}$]-human insulin.

The identity of the product was confirmed by amino acid analysis, by plasma desorption mass spectrometry and by sequential Edman degradation of the separated vinylpyridylated A- and B-chains.

EXAMPLE IX

Preparation of [Arg$^{A0}$]-des[Thr$^{B30}$]-human insulin from the precursor B(1–29)-Gly-Ser-Lys-Arg-A(1–21).

400 mg of B(1–29)-Gly-Ser-Lys-Arg-A(1–21), prepared by the methods described in examples II and VII, were dissolved in 50 ml of 50 mM tris-(hydroxymethyl)-aminomethane, 20% (by volume) ethanol adjusted to pH 10 with HCl. Sepharose ® containing 0.8 g of immobilized trypsin/ml was washed on a glass filter with the same buffer and was drained. Buffer was added to 80 g of drained gel and the volume was adjusted to 150 ml. The solution containing the precursor was added to the suspension and the mixture was left for 30 minutes at 20° C. with gentle agitation and was then filtered.

HPLC-analysis shows 50% conversion to [Arg$^{A0}$]-des-[Thr$^{B30}$]° ]-human insulin.

The gel was washed with 100 ml of buffer (without ethanol) and drained, and the proteins in the pooled filtrates were precipitated by adjusting the pH to 6. The precipitate was isolated by centrifugation and lyophilization.

The precipitate was dissolved at 4° C. in 20 ml 7M urea by adjusting the pH to 8.1 and the solution was applied to a 1.6×20 cm column of Q-Sepharose ®FF previously equilibrated at 4° C. in 20 mM tris-(hydroxymethyl)aminomethane, 7M urea adjusted to pH 8.1 with HCl. Using a flow of 40 ml/hour the column was then eluted with a linear gradient from 0 mM to 50 mM NaCl in the same buffer over 24 hours. The eluate was detected by UV-absorption and the first eluting of the two main peaks was collected. The pool was desalted in 1M acetic acid on a column of Sephadex ® G25 and was lyophilized. The yield was 145 mg of [Arg$^{A0}$]-des[Thr$^{B30}$]-human insulin.

The identity of the product was confirmed by amino acid analysis, by HPLC-analysis and by sequential Edman degradation.

EXAMPLE X

Preparation of [Arg$^{A0}$]-des[Thr$^{B30}$]-human insulin from porcine proinsulin.

40 mg of porcine proinsulin were dissolved in 800 μlitres of 0.1M HCl and 8 ml of 50 mM tris-(hydroxymethyl)aminomethane was added. A solution of 1 U Endoproteinase Lys-C from Lysobacter enzymogenes (Boehringer Mannheim) in 200 μlitres of 0.1M tris-(hydroxymethyl)aminomethane adjusted to pH 8.5 with HCl was prepared. The two solutions were mixed and were left for 16 hours at 12° C.

The reaction was stopped by adjusting the pH to 6.2 after addition of 1.8 ml 96% ethanol and the resulting suspension was left overnight at 4° C. The precipitate was isolated by centrifugation and was redissolved at 4° C. in 2 ml 7M urea by adjusting the pH to 8.1. This solution was applied to a 1.6×20 cm column of Q-Sepharose ® FF previously equilibrated at 4° C. in 20mM tris-(hydroxymethyl)aminomethane, 7M urea adjusted to pH 8.1 with HCl. Using a flow of 40 ml/hour the column was then eluted with a linear gradient from 0 mM to 50 mM NaCl in the same buffer over 24 hours. The eluate was detected by UV-absorption and the main peak was collected. The pool was desalted in 1M acetic acid on a column of Sephadex ® G25 and was lyophilized. The yield was 15 mg of [Arg$^{A0}$]-des[Thr$^{B30}$]-human insulin.

The identity of the product was confirmed by amino acid analysis, by HPLC-analysis and by sequential Edman degradation.

EXAMPLE XI

Preparation of [Arg$^{A0}$]-human insulin-(B30 amide).

200 mg of [Arg$^{A0}$]-des[Thr$^{B30}$]-human insulin prepared by one of the methods described in examples VIII to X were dissolved in a mixture containing 400 mg of threonine amide, 2.0 ml of ethanol and 0.8 ml of water. The pH was adjusted to 6.3 with acetic acid and 4 ml (settled) volume of Sepharose ® containing 3.2 mg of immobilized trypsin were added. After standing for 2 hours at 20° C. with gentle agitation, the gel was removed by filtration, and the protein was precipitated by addition of 10 volumes of 2-propanol. The air-dried precipitate was dissolved at 4° C. in 20 ml 7M urea by adjusting the pH to 8.1 and the solution was applied on a 1.6×20 cm column of Q-Sepharose ® FF previously equilibrated at 4° C. with 20 mM tris-(hydroxymethyl)aminomethane, 7M urea adjusted to pH 8.1 with HCl. Using a flow of 40 ml/hour the column was then eluted with a linear gradient from 0mM to 50mM NaCl in the same buffer over 24 hours. The eluate was detected by UV-absorption and the main peak was collected. The pool was desalted in 1M acetic acid on a column of Sephadex ® G25 and was lyophilized. The yield was 80 mg of [Arg$^{A0}$]-human insulin-(B30-amide).

The identity of the product was confirmed by amino acid analysis, by plasma desorption mass spectrometry and by sequential Edman degradation.

EXAMPLE XII

Preparation of [Gln$^{B13}$,Arg$^{A0}$]-des[Thr$^{B30}$]-human insulin.

250 mg of [Gln$^{B13}$]-B(1–29)-Ala-Lys-Arg-A(1–21), prepared by the methods described in examples III and VII, were treated with immobilized trypsin and the reaction product purified essentially as described in example VIII. The yield was 60 mg of [Gln$^{B13}$,Arg$^{A0}$]-des[Thr$^{B30}$]-human insulin.

The identity of the product was confirmed by amino acid analysis, by plasma desorption mass spectrometry and by sequential Edman degradation.

EXAMPLE XIII

Preparation of [Gln$^{A4}$, Asp$^{A21}$, Arg$^{A0}$]-human insulin-(B30-amide).

500 mg of [Gln$^{A4}$, Asp$^{A21}$]-B(1–29)-Ala-Lys-Arg-A(1–21), prepared by the methods described in examples IV and VII, were treated with immobilized trypsin and the resulting product was purified essentially as described in example VIII. The yield was 175 mg of [Gln$^{A4}$, Asp$^{A21}$, Arg$^{A0}$]-des-[Thr$^{B30}$]-human insulin.

This was converted to the B30-amide by coupling with threonine amide by the method described in example XI. The yield of purified [Gln$^{A4}$, Asp$^{A21}$, Arg$^{A0}$]-human insulin-(B30-amide) was 50 mg.

The identity of the product was confirmed by amino acid analysis, by plasma desorption mass spectrometry and by sequential Edman degradation.

EXAMPLE XIV

Preparation of [Ser$^{A21}$,Arg$^{A0}$]-human insulin-(B30-amide).

400 mg of [Ser$^{A21}$]-B(1–29)-Ala-Lys-Arg-A(1–21), prepared by the methods described in examples V and VII, were treated with immobilized trypsin and the resulting product was purified essentially as described in example VIII. The yield was 125 mg of [Ser$^{A21}$,Arg$^{A0}$]-des[Thr$^{B30}$]-human insulin.

This was converted to the B30-amide by coupling with threonine amide by the method described in example XI. The yield of purified [Ser$^{A21}$,Arg$^{A0}$]-human insulin-(B30-amide) was 40 mg.

The identity of the product was confirmed by amino acid analysis, by plasma desorption mass spectrometry and by sequential Edman degradation.

EXAMPLE XV

Preparation of [Arg$^{B27}$,Arg$^{A0}$]-des [Thr$^{B30}$]-human insulin.

250 mg of [Arg$^{B27}$]-B(1–29)-Ala-Lys-Arg-A(1–21), prepared by the methods described in examples VI and VII, were treated with immobilized trypsin and the resulting product was purified essentially as described in example VIII. The yield was 50 mg of [Arg$^{B27}$,Arg$^{A0}$]-des [Thr$^{B30}$]-human insulin.

The identity of the product was confirmed by amino acid analysis and by sequential Edman degradation.

EXAMPLE XVI

Formulation of an injectable prolonged acting preparation containing dissolved [Arg$^{A0}$]-human insulin-(B30-amide).

60 μmoles of [Arg$^{A0}$]-human insulin-(B30-amide) was dissolved in 4 ml of 0.1M HCl and 20 ml of 1.5% m-cresol were added. The solution was mixed with 70 ml of 1% NaCl and 3.25 ml 0.1M ZnCl$_2$ and the pH was adjusted to 4.0. The volume was finally adjusted to 100 ml with water and sterilized by filtration.

EXAMPLE XVII

Formulation of an injectable prolonged acting preparation containing a crystalline suspension of [Arg$^{A0}$]-human insulin-(B30-amide).

60 μmoles of [Arg$^{A0}$]-human insulin-(B30-amide) were dissolved in 70 ml of 1% NaCl solution containing 0.5% m-cresol by adjusting the pH to 9.7 with 1M NaOH and 325 μlitres of 0.1M zinc acetate were added. After readjustment of the pH to 9.7, the volume was adjusted to 80 ml with water and the solution was sterilized by filtration. 20 ml of 65mM NaH$_2$PO$_4$ containing 0.3% m-cresol and adjusted to pH 6.0 with NaOH were sterilized by filtration.

Under sterile conditions the two solutions were mixed and the resulting suspension was left at 20° C. for 1 hour with very gentle stirring. The pH was finally adjusted to 7.3 with HCl.

EXAMPLE XVIII

Demonstration of prolongation after subcutaneous injection in rats by external gamma-counting.

For the experiments female Wistar rats of approx. 250 g body weight and more than 90 days old were used. The rats were acclimatized for about one week before use and were fed ad libitum. For four days prior to the experiments, the rats had a 20 mM aqueous solution of potassium iodide as drinking water.

The test preparations were:
  I. Suspension preparation containing [Arg$^{A0}$]-human insulin-(B30-amide) and prepared according to example XVII.
  II. Solution preparation containing [Arg$^{A0}$]-human insulin (B30-amide) and prepared according to example XVI.
  III. A fast acting solution preparation containing semisynthetic human insulin (Velosulin®, 100 U/ml).

All three formulations were additionally containing 50 μCi/ml [mono-$^{125}$I]-insulin or -insulin compound tracer, respectively, prepared by standard radioiodination methods.

The rats were injected subcutaneously at the back of the thigh with 50 μlitres preparation containing 3.5 nmol insulin compound and 2.5 μCi [$^{125}$I]-labelled tracer. During the study period the rats were immobilized in rat holders.

The disappearance of the tracer from the injection sites, which is a measure for the absorption of the insulin compound from the subcutaneous depot (C. Binder: Absorption of Injected Insulin. Munksgaard, Copenhagen 1969), were measured using two stationary MIP-10 ratemeters and detectors E749 with 3 mm NaI scintillation crystals with Be-windows and collimators with 60° visual angle and 10 mm openings (Raytronic). The ratemeters were connected with Mini recorders 121N (Raytronic). The detectors were fixated two cm above the skin at the injection sites. The radioactivity was monitored over a five minute period at 0, 0.5, 1, 1.5, 2, 2.5, 3, 4, 5, 6, 8, 12 and 24 hours after the injection of the preparation. After subtraction of background counts, the count rates were converted to percentages of the initial count rate.

In FIG. 3 the mean values of the residual radioactivity are shown as function of time for each preparation. Taking the time for 50% residual activity (T50%) as a measure for the prolongation, it is found from the curves:

|  | T$_{50\%}$ |
|---|---|
| Prep. I | >12 h |
| Prep. II | ≈8 h |
| Prep. III | ≈0.5 h |

These results show that both of the preparations containing [Arg$^{A0}$]-human insulin-(B30-amide) show pronounced prolongation compared to the fast acting human insulin preparation.

EXAMPLE XIX

Formulation of an injectable prolonged acting preparation containing a solution of [Arg$^{A0}$,Arg$^{B27}$]-des[Thr$^{B30}$]-human insulin.

12 μmoles of [Arg$^{A0}$,Arg$^{B27}$]-des[Thr$^{B30}$]-human insulin were dissolved in 35 ml of 1% NaCl solution containing 0.5% m-cresol by adjusting the pH to 3.5 with 1 M HCl and 650 μlitres of 0.1M zinc acetate were added. After readjustment of the pH to 3.5, the volume was adjusted to 50 ml with water and the solution was sterilized by filtration.

EXAMPLE XX

Demonstration of prolonged effect in rabbits after subcutaneous injection.

The degree of prolongation of a solution preparation containing 0.24 mM [Arg$^{A0}$,Arg$^{B27}$]-des[Thr$^{B30}$]-human insulin prepared according to example XIX was determined in rabbits according to the method described in British Pharmacopoeia, 1980. 65 μlitres of preparation were injected subcutaneously in six rabbits, and blood samples were collected for glucose determination immediately before injection and at 1, 2, 4 and 6 hours after the injection. The glucose values were expressed as percent of the value before the injection.

The determination showed the following mean values:

| Time after injection: | 0h | 1h | 2h | 4h | 6h |
|---|---|---|---|---|---|
| % glucose of initial: | 100% | 68.2% | 65.0% | 80.1% | 79.4% |

By determination of the index of prolongation according to the method described in J. Markussen et al: Protein Engineering vol. 1 no.3 pp.205-213 (1987) a value of 42 was calculated. By comparison with the results in table 1, ibid. the solution preparation containing [Arg$^{A0}$,Arg$^{B27}$]-des[Thr$^{B30}$]-human insulin is found to have the same prolongation as the commonly used prolonged acting zinc insulin suspension preparation Actrapid ® Human.

We claim:

1. A purified insulin compound of formula:

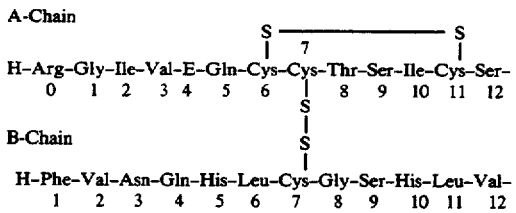

-continued

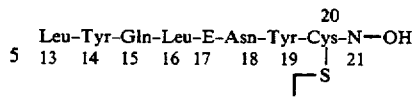

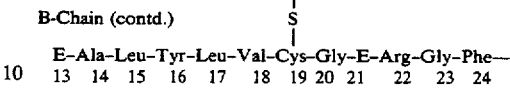

B-Chain (contd.)

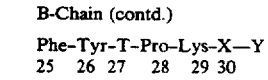

wherein
E is independently Glu or a neutral amino acid residue which can be coded for by nucleotide sequences;
N is an amino acid residue which can be coded by nucleotide sequences;
T is Thr or Arg;
X is Thr, Set, Ala or OH; and
Y is OR or NR$^1$R$^2$ wherein R, R$^1$ and R$^2$ independently are hydrogen or C$_{1-6}$-alkyl, provided that Y is not present when X is OH and that at least one of E, N and T is an amino acid residue different from the corresponding residue of human insulin when Y is OH.

2. The purified insulin compound according to claim 1, wherein
E is independently Glu or Gln;
N is Asn, Asp, Ser or Gly;
T is Thr or Arg;
X is Thr; and
Y is NH$_2$.

3. The purified insulin compound according to claim 2, wherein E is Glu, N is Ash, T is Thr, X is Thr and Y is NH$_2$.

4. The purified insulin compound according to claim 2, wherein E is Glu, N is Ser, T is Thr, X is Thr and Y is NH$_2$.

5. The purified insulin compound according to claim 1, wherein E in position B13 is Gln, E in the other positions is Glu, N is Ash, T is Thr, X is Thr and Y is NH$_2$.

6. The purified insulin compound according to claim 1, wherein E in position A4 is Gln, E in the other positions is Glu, N is Asp, T is Thr, X is Thr and Y is NH$_2$.

7. The purified insulin compound according to claim 1, wherein E is Glu, N is Asn, T is Arg and X is OH.

8. A purified insulin compound which is [Arg$^{A0}$]-des[Thr$^{B30}$]-human insulin.

9. A purified insulin compound which is [Arg$^{A0}$]-human insulin (B30 amide).

10. A purified insulin compound which is [Arg$^{A0}$, Ser$^{A21}$]-human insulin (B30 amide).

11. A purified insulin compound which is [Arg$^{A0}$, Gln$^{B13}$]-human insulin (B30 amide).

12. A purified insulin compound which is [Arg$^{A0}$,Gln$^{A4}$, Asp$^{A21}$]-human insulin (B30 amide).

13. A purified insulin compound which is [Arg$^{A0}$, Arg$^{B27}$]-des [Thr$^{B30}$]-human insulin.

14. An insulin preparation comprising a solution of a purified insulin compound according to claim 1 in an aqueous medium which is isoosmotic with blood serum and has a pH between 2 and 5.5.

15. The insulin preparation according to claim 14, further comprising a buffer.

16. The insulin preparation according to claim 14, further comprising a preserving agent.

17. The insulin preparation according to claim 14, further comprising a fast acting insulin.

18. An insulin preparation comprising a solution of a purified insulin compound selected from the group consisting of:

[Arg$^{40}$]-des [Thr$^{B30}$]-human insulin
[Arg$^{40}$]-human insulin (B30 amide)
[Arg$^{40}$, Ser$^{A21}$]-human insulin (B30 amide)
[Arg$^{40}$, Gln$^{B13}$]-human insulin (B30 amide)
[Arg$^{40}$, Gln$^{A4}$, Asp$^{A21}$]-human insulin (B30 amide) and
[Arg$^{40}$, Arg$^{B27}$]-des [Thr$^{B30}$]-human insulin.

* * * * *